United States Patent [19]

Scangos et al.

[11] Patent Number: 5,015,570

[45] Date of Patent: May 14, 1991

[54] MOLECULAR DIAGNOSIS OF ALZHEIMER DISEASE

[75] Inventors: George A. Scangos, Woodbridge; Peter M. M. Rae, Hamden; Axel J. Unterbeck, West Haven; Michael E. Kamarck, Bethany, all of Conn.

[73] Assignee: Molecular Therapeutics, Inc., West Haven, Conn.

[21] Appl. No.: 194,053

[22] Filed: May 13, 1988

[51] Int. Cl.[5] .................... C12Q 1/68; G01N 33/533
[52] U.S. Cl. ........................................ 435/6; 436/501; 436/811; 536/27; 935/19; 935/77; 935/78
[58] Field of Search ............... 435/6; 436/501, 811; 536/27; 935/19, 77, 78

[56] References Cited

U.S. PATENT DOCUMENTS 4,666,829  5/1987  Glenner et al. .................... 435/6

OTHER PUBLICATIONS

Kang et al., (1987) Nature, vol. 325, pp. 733-736.

*Primary Examiner*—Robert A. Wax
*Assistant Examiner*—Ardin H. Marschel
*Attorney, Agent, or Firm*—Sprung Horn Kramer & Woods

[57] ABSTRACT

A method for diagnosing Alzheimer Disease or a predisposition to develop Alzheimer Disease in an individual, by determining the presence of an alteration in the normal base sequence of the 24 base pairs appearing at the end of the APC coding sequence of the preAPC gene, or in the normal base sequence of the corresponding mRNA, in the DNA or RNA or such individual. The method detects the presence of a frameshift mutation in the preAPC gene postulated to result in the synthesis of the APC protein. Accumulation of APC protein in the brain is a phenomenon of Alzheimer Disease. A variety of nucleic acid hybridization techniques are applicable to the determination of an alteration in the preAPC gene sequence of interest.

20 Claims, 1 Drawing Sheet

```
... GAA GUG AAG AUG GAU GCA GAA UUC CGA CAU GAC UCA GGA UAU GAA
            Met Asp Ala Glu Phe Arg His Asp Ser Gly Tyr Glu
             1

GUU CAU CAU CAA AAA UUG GUG UUC UUU GCA GAA GAU GUG GGU UCA AAC
    Val His His Gln Lys Leu Val Phe Phe Ala Glu Asp Val Gly Ser Asn a        b    c
    AAA GGU GCA AUC AUU GGA CUC AUG GUG GGC GGU GUU GUC AUA GCG ACA
    Lys Gly Ala Ile Ile Gly Leu Met Val Gly  Gly Val Val Ile Ala
                                          37          40

GUG AUC GUC AUC ACC UUG GUG AUG CUG AAG AAG AAA ...
    44
```

FIG. 1

```
... GAA GUG AAG AUG GAU GCA GAA UUC CGA CAU GAC UCA GGA UAU GAA
            Met Asp Ala Glu Phe Arg His Asp Ser Gly Tyr Glu
             1

GUU CAU CAU CAA AAA UUG GUG UUC UUU GCA GAA GAU GUG GGU UCA AAC
Val His His Gln Lys Leu Val Phe Phe Ala Glu Asp Val Gly Ser Asn a       b       c
AAA GGU GCA AUC AUU GGA CUC AUG GUG GGC GGU GUU GUC AUA GCG ACA
Lys Gly Ala Ile Ile Gly Leu Met Val Gly Gly Val Val Ile Ala
                                    37          40

GUG AUC GUC AUC ACC UUG GUG AUG CUG AAG AAG AAA ...
44
```

FIG. 2

```
(a) GUG GGG GUG UUG UCA UAG CGA CAG UGA UGC ...
    Val Gly Val Leu Ser  *

(b) GUG GGC GGU GUU GUG UCA UAG CGA CAG UGA UCG ...
    Val Gly Gly Val Val Ser  *

(c) GUG GGC GGU GUU GUC UAG CGA CAG UGA UCG ...
    Val Gly Gly Val Val   *
                    40
```

MOLECULAR DIAGNOSIS OF ALZHEIMER DISEASE

BACKGROUND OF THE INVENTION

This invention relates to the diagnosis of Alzheimer Disease in human patients. The invention further relates to assessing the predisposition of a presymptomatic individual to develop the disease. More particularly, the present invention concerns the use of nucleic acid probes to detect gene alterations relating to Alzheimer Disease.

Alzheimer Disease is a progressive, degenerative disease of the central nervous system, characterized by specific neuropathological lesions. Many neuronal perikarya contain accumulations of neurofibrillary tangles (NFT), which are composed of paired helical filaments (PHF). Neurofibrillary tangles contain a protein structurally different from the amyloid found in extracellular aggregates in amyloid plaque cores and in cerebrovascular lesions of congophilic angiopathy. Similar amyloid lesions occur in such pathological conditions as Down Syndrome, Gerstmann-Straeussler-Scheinker Syndrome, Kuru, and in a minority of patients with Creutzfeldt-Jakob Disease.

A genetic component is indicated by large scale studies of pedigrees in which ten or more members of four generations have developed a dementia of the Alzheimer type before they were 70 years old. In such cases, it appears that an aberrant gene is transmitted as autosomal dominant. Most cases of Alzheimer Disease occur in people over 80 years of age, and it has been calculated that up to 30% of the Caucasian population over the age of 85 has the disease.

It is estimated that Alzheimer Disease currently affects over 2 million elderly people in the U.S. Because the disorder is usually late onset, the number of affected individuals will continue to grow as the elderly population increases in size. There are currently more than 25 million people in the U.S. over the age of 65, and this number will more than double by the year 2025.

One of the major biochemical symptoms in the cerebral cortex of Alzheimer patients is the appearance in plaque and blood vessel deposits of a protein known as the amyloid plaque core (APC) protein. This protein is an insoluble, highly aggregating, small polypeptide of relative molecular mass 4,500. APC has been understood to have 40–42 amino acids, and is currently believed more likely to be 40 amino acids in length. This polypeptide is also deposited in the brains of relatively older individuals with trisomy 21 (Down Syndrome). Kang et al, Nature 325, 733–736, 1987, propose that the amyloid protein is of neuronal origin and is part of a larger precursor protein. To identify this precursor, a full-length complementary DNA clone coding for the APC protein was isolated and sequenced. The predicted precursor consists of 695 residues and contains features characteristic of glycosylated cell-surface receptors. This cDNA sequence, together with the localization of its gene in chromosome 21, suggests that the cerebral amyloid deposited in Alzheimer Disease and aged Down Syndrome is caused either by aberrant catabolism of a cell-surface receptor, or by aberrant synthesis or processing of its mRNA. In order to determine patterns of expression of the gene in brain, APC cDNA was hybridized to tissue sections of the mouse nervous system. Amyloid precursor protein mRNA was detected in most neurons of the central and peripheral nervous system.

A means for early and accurate diagnosis of Alzheimer Disease will have a major impact on the progress of research on dementia. Because no peripheral biochemical marker for Alzheimer Disease has been found, a definitive diagnosis of the disorder can be made only if histologic confirmation is obtained by performance of a cerebral biopsy or an autopsy. Despite the fact that Alzheimer Disease is essentially an untreatable condition, there would be significant value to know whether or not an individual with Alzheimer symptoms in fact has the disease. A number of treatable conditions are characterized by symptoms similar to those found in patients with Alzheimer Disease. Some such treatable conditions are brain tumors, thyroid and other endocrine dysfunctions, depression, infection, vitamin and mineral deficiencies, metabolic disorders, unrecognized injuries, and side effects of medication. The medical literature advises physicians to conduct a thorough examination, medical history, and testing in order to rule out reversible disorders before diagnosing the untreatable Alzheimer condition.

SUMMARY OF THE INVENTION

The present invention provides a method for diagnosing Alzheimer Disease in an individual with symptoms, or for assessing a predisposition to develop the disease in a presymptomatic individual, based on a determination of the presence of an alteration in the normal DNA or mRNA of such individual. The genetic region of interest is the 24 base pair sequence appearing at the end of the APC coding sequence of the preAPC gene or in the normal sequence of the corresponding mRNA. Using nucleic acid hybridization techniques, the presence of any alteration or the presence of a specific alteration in such 24 base sequence can be detected and aid in the diagnosis of Alzheimer Disease.

According to the present invention, the production of the APC protein implicated in Alzheimer Disease is the result of a mutation in the region of the gene that encodes the carboxy terminus of the peptide. A frameshift mutation in that region is seen as introducing two translation termination signals adjacent to the terminus of the APC protein coding region in the preAPC gene. In addition, a strong translation initiation site is seen in the region of the gene just preceeding the APC protein coding sequence so that the introduction of a frameshift in close proximity results in repeated translation of just the region of the precursor protein corresponding to the APC protein. This would account for the overproduction of the APC protein in patients afflicted with Alzheimer Disease.

From the known sequence of the preAPC gene, the normal sequence, which if altered introduces a frameshift mutation, constitutes the following 24 base sequence:

5' GGC GGT GTT GTC ATA GCG ACA GTG 3', as the sense strand (herein referred to as the normal sense sequence), and

5' CAC TGT CGC TAT GAC AAC ACC GCC 3', as the antisense strand (herein referred to as the normal antisense sequence). The complementary mRNA sequence is:

5' GGC GGU GUU GUC AUA GCG ACA GUG 3', herein referred to as the normal complementary RNA sequence. Hybridization techniques which permit detection of an alteration in the sequence of any of these three normal DNA and RNA sequences will be applicable to the present invention.

BRIEF DESCRIPTION OF THE DRAWINGS

FIG. 1 illustrates the portion of the preAPC gene sequence that includes the region coding for the APC protein. The discussion below explains the translational effects of frameshift mutations in the 24 base sequence at the end of such coding region.

FIG. 2 illustrates +1 and −2 frameshifts that result in creation of a stop codon just following the coding sequence for the APC protein.

DESCRIPTION OF THE PREFERRED EMBODIMENTS

Based on DNA sequence analysis of the preAPC cDNA clone (Kang, J. et al, supra), and on information from studies of protein synthesis in cells transfected with mutated drug resistance genes (Thomas and Capecchi, Nature 324, 34–38, 1986), the present invention views the synthesis of the APC protein from preAPC mRNA as the consequence of a frameshift mutation in the APC coding portion of the gene. This frameshift, which is detectable by oligonucleotide probes, provides the basis for pre- and post-symptomatic diagnostic tests for Alzheimer Disease.

A mutation in the region of the gene that encodes the carboxy terminus of the peptide would result in the production of the APC protein. A −1 or +2 frameshift mutation in that region results in the introduction of two translation termination signals immediately 3' to the terminus of the APC protein. FIG. 1 demonstrates how two termination codons are introduced as a result of such mutations. The upper line of each pair is the triplet code in messenger RNA, and the lower line is the amino acid sequence. The Asp number 1 is the first amino acid of the APC protein, and the Val number 40 is presently considered the last amino acid of APC. APC production from preAPC mRNA involves small deletion or insertion mutations at or near the end of the APC coding region that have the effect of moving a translation stop codon into the preAPC reading frame. The two out-of-frame stop codons that are potential terminators of translation in the synthesis of APC are the underlined UA G and UG A sequences. Possible sites of a single base deletion that would put the UAG and UGA in reading frame are indicated by the lower case letters a and c; a possible site of a two base insertion having the same effect is indicated by the lower case letter b. FIG. 2 shows specific frame shift mutations corresponding to a, b and c above and depicted in FIG. 1 that introduce premature stop codons in the preAPC mRNA.

The above described conditions would account for the termination of mRNA translation at the end of the preAPC gene corresponding to the C-terminus of the APC protein. Studies of both E. coli and cultured mammalian cells (Johansen et al, Proc. Natl. Acad. Sci. USA 81, 7698–7702, 1984; Liu et al, Nature 309, 82–85, 1984; Thomas and Capecci, supra) suggest that upon translation termination ribosomes can scan an mRNA both forward and backward for a nearby AUG and can reinitiate translation at that point. There is a strong initiation site just preceeding the APC protein (see FIG. 1), so that the introduction of the frameshift would result in repeated translation of just the region of the precursor encoding the APC protein.

Accordingly, the effect of a −1 or +2 type of frameshift mutation at or near the portion of the preAPC gene sequence coding for the carboxy terminus of APC is the introduction of one or two in-frame translation termination signals, one at what would be amino acid 41 of APC, and the other at what would be amino acid 44. Ribosome scanning of the preAPC mRNA in the vicinity of these termination signals will identify an AUG that is about 125 nucleotides upstream of the termination signals. This AUG codon for methionine is the triplet that immediately preceeds the codon for the N-terminal amino acid of amyloid plaque core protein. Since eukaryotic protein synthesis is usually initiated with a methionine that is subsequently removed from a protein, the present invention contemplates a "frameshift-termination-reinitiation" model of APC production from within a large open reading frame in a 3.4 kb mRNA.

Further, it is known that the nucleotide sequence context of the Met codon (AAG AUG G) constitutes a most favored eukaryotic translation initiation site according to Kozak (Cell 44, 283–292, 1986), who found the optimum context to have an A at position −3, and a G at position +4. This condition is fulfilled at the AUG in question, and in fact is not at the preAPC initiator codon.

The portion of the preAPC gene in which the frameshift mutation discussed above is contemplated to occur is between nucleotides 1897 and 1921 of the cDNA sequence published by Kang et al, supra. Number 1921 is the third position of the downstream member of the pair of −1 frame nonsense triplets, and any insertion or deletion beyond this point would result in expression of a polypeptide longer than the known APC protein. Number 1897 is the first position of amino acid 37 of the APC protein, which is the first of the half-dozen carboxy terminus amino acids for which protein sequence results have been ambiguous; the amino acid sequence upstream of no. 37 is unambiguous and in perfect agreement with the amino acid sequence reverse translated from the normal brain preAPC cDNA sequence.

Therefore, the alteration in the preAPC coding sequence that is of diagnostic significance will appear in the 24 base sequence beginning with glycine 37 and ending with the codon in position 43 (see FIG. 1). The compositions of the normal sense and antisense DNA sequences, and of the complementary mRNA sequence, are as set out above. Accordingly, the present method comprises the step of determining the presence of an alteraction in the normal antisense DNA sequence, i.e.,

5' CAC TGT CGC TAT GAC AAC ACC GCC 3', or its normal complementary sense sequence or its normal complementary RNA sequence (the translated mRNA sequence).

It will be apparent to those working in the field of nucleic acid hybridization that a number of different approaches and methodologies can be applied to the task of determining an alteration in the 24 base sequence of interest. Any technique that detects either the presence of a specific mutuation in the sequence or the presence of any mutation in the sequence can be applied to the present invention.

A particularly preferred approach to simply and accurately screen samples of DNA or RNA for mutations causative of APC overproduction is based on the principle that a normal preAPC gene probe that hybridizes with DNA from a normal individual will anneal perfectly base-for-base with complementary sequences in the sample, and will thus be insensitive to the action of certain nucleic acid-digesting enzymes. If, on the other hand, there is a mutant allele of the preAPC gene in the sample, the probe will hybridize imperfectly, leaving mismatched base pairs that will render the probe sensitive to some detectable degree of digestion by nuclease enzymes.

Because Alzheimer Disease is understood to be the result of a dominant gene effect, it is necessary to adopt an analytical procedure that is capable of distinguishing the presence of a mutated allele in the presence of the normal allele. It is not appropriate, as it would be in the case of a recessive genetic disorder, to analyze the sample for the presence of the normal allele unless the technique used can assure that all alleles present are detected. Accordingly, it will generally be preferred to focus on detection of the mutated allele since the presence of any such allele indicates the presence of the dominant effect whether in heterozygous or homozygous individuals.

A straightforward approach to detecting any mutation in the normal gene sequence is to use a probe, usually an oligonucleotide probe, representing the normal gene sequence to determine if there are sequences in a DNA or messenger RNA sample that are incompletely homologous with the probe due to an insertion or a deletion mutation. This approach does not require knowledge of the particular mutation(s), and will also be more sensitive than one involving multiple very similar probes.

In such a method, sample DNA or RNA from the patient is obtained in a single stranded form, i.e., double stranded DNA is appropriately and conventionally denatured whereas mRNA exists already in single stranded form, and hybridized with an oligonucleotide probe comprising any one, or a combination, of the four sequences: the normal sense or antisense DNA sequence or the two corresponding RNA sequences. Thereafter, resulting hybrids are analyzed for imperfect homology. The probe in such method will preferably consist of the exact 24 base sequence of the normal sense or antisense DNA sequences or the corresponding RNA sequences, however, can be up to about 30, or even about 50 or more, nucleotides long and can be of any nucleotide content consistent with the analytical method to be used. Conversely, the probe can consist of as few nucleotides as needed to accurately analyze for imperfect homology using the selected analytical method for the hybridization and provided the region of mutation in the 24 base sequence is probed, e.g., greater than about 10, and preferably 12, or better 17–19, or more bases. Ways in which incomplete homology can be detected for the purpose of diagnosing heritable Alzheimer Disease include: (1) analysis of hybrids between labelled probe and sample DNA by exposure to a single stranded specific nuclease such as $S_1$ nuclease or mung bean nuclease, (2) differential thermal melting of perfect and imperfect DNA hybrids, (3) nuclease analysis of hybrids between labelled probe and sample RNA, and (4) direct sequencing of nucleic acids representing the genomic sequence of interest.

DNA samples for a genetic presymptomatic or predisposition test for Alzheimer Disease can be obtained from any body tissue, since inherited mutations are present in the DNA of all cell nuclei. However, it will be preferrable to obtain samples in the least invasive way, such as through the collection of a few milliliters of blood for leukocyte DNA.

(1) Nuclease analysis

The simplest and most sensitive assay for an altered APC sequence in a DNA sample will be one in which (i) the sample DNA is denatured then hybridized with the end labelled normal gene oligonucleotide probe; (ii) the mixture is treated with nuclease to destroy unhybridized probe and to clip partially hybridized probe at points where there is as little as a single base pair mismatch with sample DNA; then (iii) the mixture is denatured and subjected to high resolution acrylamide gel electrophoresis or HPLC to analyze the labelled probe.

Perfectly hybridized normal gene probe will be insensitive to nuclease digestion and will retain its 24 nucleotide length; unhybridized probe will be degraded by the enzyme and the label will be in mononucleotides; probe that hybridized imperfectly to a mutant allele of the gene will be clipped at the point of mismatch wherever it may be along the length of the probe, and this will be reflected in, for example, an electrophoretic mobility shift of the end labelled element. The radioactive products of hybridization/nuclease treatment involving normal DNA will be 24-mers, while the products of a procedure involving DNA from an individual with one normal gene and one Alzheimer Disease allele will be 24-mers and oligonucleotides with some shorter length reflecting the distance between the 5' labelled end of the probe and the exact site of the mutation that caused the mismatch.

(2) Differential melting

It is possible to distinguish (i) perfectly matched hybrids involving oligonucleotides and complementary sequences in genomic DNA from (ii) hybrids in which one or more base pairs are improperly matched by comparing the temperatures at which (i) and (ii) denature. Perfectly matched hybrids are more thermostable than those in which some bases are unpaired, and this is reflected in a higher $T_m$ (midpoint of a melting curve) of the former. In principle, the melting curve of hybrids between the Alzheimer Disease oligonucleotide probe and DNA from a normal individual could be distinguished from the melting curve of hybrids between the oligonucleotide probe and DNA from an individual carrying an Alzheimer Disease allele. However, the fact that heterozygotes express the disease means that half of the hybrids will melt with a normal profile, and this could limit the sensitivity of an assay based on differential melting.

(3) Screening messenger RNA samples for the familial defect

An alternative to the analysis of DNA in looking for sequence alterations underlying APC production is the hybridization of oligonucleotide probes to preAPC mRNA in cytoplasmic RNA. This approach requires that easily obtained cells such as leukocytes express preAPC mRNA, since it is seen as impractical to have to obtain neuronal material for RNA. In this regard, there is good evidence that the preAPC gene is expressed in many diverse tissues, and not just in brain. The reason for interest in an examination of preAPC mRNA for mutations rather than the preAPC gene itself is that it is also contemplated that the mutations causing premature translation termination of the preAPC mRNA and accumulation of APC in brain can be introduced at the RNA level through a genetically directed RNA processing defect such as abnormal splicing. Such a heritable defect of preAPC mRNA would not necessarily be detectable in the preAPC gene itself. Procedures for the examination of mRNA using oligonucleotide probes are essentially the same as for DNA analysis, particularly the nuclease sensitivity analysis.

Where labeled probes are used, the label can be any of those conventionally known or as developed in the art hereafter. Useful conventional labels are radioisotopes, fluorescers, chemiluminescers, or specifically bindable ligands such as haptens and biotin which can be detected by binding with an appropriately labeled antibody or other binding protein, e.g., avidin.

An alternative to probing the same nucleic acid with the normal sequences is to analyze for specific mutations in the 24 base sequence. Again, a variety of techniques will be evident to the worker in the field. Depending upon the knowledge of the site(s) of mutation, up to 24 different probes representing individual possible mutant alleles can be used in a yes-or-no DNA hybridization assay to scan the region for any base pair differences from normal. Of course, only a single probe is needed where a particular mutation has been identified. An oligonucleotide probe used in this approach will consist essentially of at least 10 nucleotides whose base sequence is homologous with the DNA sequence of the preAPC gene having a mutation in the 24 base normal sequence or in its complementary DNA or RNA sequences. The probe will have a length optimized or allowed by the technique of analysis and can consist essentially of the mutated 24 base sequence itself.

(4) Direct Nucleic Acid Sequencing

An alternative to the preceding indirect approaches to obtaining nucleic acid sequence information is to amplify the relevant genetic region in vitro and directly sequence the amplified nucleic acids using standard sequencing protocols. Amplification can be achieved in a variety of ways, including, for example, subcloning in a procaryotic vector or through the performance of polymerase chain reactions.

The present invention will now be illustrated, but is not intended to be limited, by the following examples.

EXAMPLES

A. Probing Genomic DNA Samples

1. Oligonucleotide probe preparation: The normal gene nucleotide sequence of the region 1897 to 1921 is:

5' GGC GGT GTT GTC ATA GCG ACA GTG 3'
(#1), with the complementary sequence being

3' CCG CCA CAA CAG TAT CGC TGT CAC 5'
(#2).

Either (#1) or (#2) is the preferred composition of a chemically synthesized oligonucleotide probe. For tagging, the probe could be 5' end labelled with $^{32}P$ using polynucleotide kinase (Wallace, Cold Spring Harbor Symp. Quant. Biol. 51, 257-261, 1986), or the probe could be synthesized and isotopically labeled in a primer extension reaction (Dattagupta et al, BioTechn. 5, 38-43, 1987). The probe could also be labelled non-isotopically (Jablonski et al, Nucl. Acids Res. 14, 6115-6128, 1986).

2. Sample DNA preparation: DNA is most readily obtained from white blood cells, and a few ml or less of blood provides sufficient DNA for analysis. The DNA is extracted from tissues by standard procedures involving detergent lysis of cells, and removal of protein by enzymatic digestion and/or treatment of the lysate with organic solvents (Rae and Franke, Chromosoma 39, 443-456, 1972). DNA is recovered from the aqueous phase of the extract by ethanol precipitation, then is redissolved in water or a Tris-EDTA solution.

3. Sample DNA denaturation, addition of the probe, and annealing: Mix about 5 µg of sample DNA with about 50 ng of labelled oligonucleotide probe in a volume of 20 µl $H_2O$; boil for 5 minutes to denature the sample DNA, then add 10 µl of 0.1M Tris, pH 8, 3M NaCl. Incubate the mixture at 50° for two hours for hybridization.

4. Treatment with nuclease to completely degrade unhybridized probe, and to modify the length of any partially hybridized probe by clipping at sites of base pair mismatches between probe and sample: One procedure that has been used to map regions of homology between nucleic acid samples (Kohorn and Rae, Proc. Natl. Acad. Sci. USA 80, 3265-3268, 1983) is to (i) dilute hybridizations to 250 µl in 30 mM NaOAc, 5 mM $ZnSO_4$, pH 4.5, (ii) add 50-300 U $S_1$ nuclease and incubate reactions at room temperature for 1 hour, (iii) stop digestions by addition of 50 µl of 0.5M Tris, pH 9.5, 0.1M EDTA, and, after addition of 20 µg of E. coli tRNA as carrier, precipitate surviving nucleic acids in ethanol.

5 Gel electrophoresis or thin layer chromatography display of the products of nuclease treatment, after denaturation to release hybridized probe: For example, following resuspension of pellets in 3-5 µl of 0.1M NaOH, 1 mM EDTA, add an equal volume of 80% formamide, 0.03% bromphenol blue, 0.03% xylene cyanol, for electrophoresis in thin 20% denaturing acrylamide gels, looking for full length probe plus or minus probe molecules of shorter length:

|  | homozygous normal | heterozygous AD | homozygous AD |
| --- | --- | --- | --- |
| 24-mer | + | + | − |
| <24-mer | − | + | + |

6. Detection of radioactive probe can be by autoradiography or scintillation spectrometry. Non-isotopically labelled probe can be detected colorimetrically or by chemiluminescence, for example.

B. Probing Cytoplasmic RNA Samples

1. Oligonucleotide probe preparation: The location of the mutant stop codon in the mRNA would necessarily be in the same region as discussed above, so that the same oligonucleotide would be used to probe sample mRNAs as would be used to probe sample DNAs (only oligo #2, however, since it is the one complementary to the single stranded RNA).

2. Sample RNA preparation: RNA is most readily prepared from white blood cells, and a few ml of blood provides sufficient RNA for analysis. The RNA is extracted from cells by standard procedures involving detergent lysis, and removal of DNA and protein by enzymatic digestion and treatment of the lysate with organic solvents (Murtif and Rae, Nucl. Acids Res. 13, 3221-3239, 1985). RNA is recovered from the aqueous phase of the extract by ethanol precipitation, then is redissolved in water.

3. Addition of the probe, and annealing: For hybridization, RNA (generally about 3 μg) and labelled oligonucleotide probe (generally, about 50,000 cpm) are combined in 30 μl of 40% formamide, 4 × SSC, 33 mM Na$_2$HPO$_4$—KH$_2$PO$_4$, pH 7.0, and incubated for at least 8 hours at 37°.

4., 5. and 6. These steps are the same as steps 4., 5. and 6. in Part A above.

What is claimed is:

1. A method for diagnosing Alzheimer Disease or a predisposition to develop Alzheimer Disease in an individual, comprising the step of determining the presence of an alteration in the normal DNA base sequence

5' CAC TGT CGC TAT GAC AAC ACC GCC 3', or its normal complementary DNA or RNA sequences, in a sample of the DNA or RNA of such individual by hybridization with an oligonucleotide probe.

2. The method of claim 1 wherein such individual is presymptomatic for Alzheimer Disease and the presence of an alteration in said normal DNA base sequence, or in its complementary DNA or RNA sequences, indicates a risk that such individual will develop the disease.

3. The method of claim 1 wherein the presence of an alteration in said normal sequences is determined by obtaining sample DNA or RNA from said individual in single stranded form, hybridizing the single stranded sample DNA or RNA with an oligonucleotide probe comprising the DNA base sequence

5' CAC TGT CGC TAT GAC AAC ACC GCC 3' or its corresponding RNA base sequence, or their complementary DNA or RNA sequences, and analyzing resulting hybrids for imperfect homology.

4. The method of claim 3 wherein said oligonucleotide probe consists of less than 50 nucleotides and includes the 24 nucleotide DNA base sequence

5' CAC TGT CGC TAT GAC AAC ACC GCC 3', or its corresponding RNA base sequence, or their complementary DNA or RNA sequences.

5. The method of claim 4 wherein said oligonucleotide probe consists essentially of less than 30 nucleotides.

6. The method of claim 4 wherein said oligonucleotide probe consists essentially of only said 24 nucleotide base sequence.

7. The method of claim 3 wherein imperfect homology in said resulting hybrids is determined by exposing the hybrids to a single stranded specific nuclease and detecting the presence or absence of hybrid fragments.

8. The method of claim 1 wherein the presence of an alteration in said normal sequences is determined by obtaining sample DNA or RNA from said individual in single stranded form, hybridizing the single stranded sample DNA or RNA with an oligonucleotide probe having a base sequence of at least 10 nucleotides homologous with the DNA sequence of the preAPC gene having a mutation in said normal DNA base sequence or in its complementary DNA or RNA sequence, and analyzing resulting hybrids for perfect homology.

9. The method of claim 8 wherein said oligonucleotide probe consists essentially of up to 24 nucleotides corresponding to the base sequence of said mutated form of the normal DNA base sequence or its complementary DNA or RNA sequences.

10. The method of claim 1 wherein the sample is genomic DNA.

11. The method of claim 1 wherein the sample is mRNA.

12. An oligonucleotide probe for use in the diagnosis of Alzheimer Disease or a predisposition to develop Alzheimer Disease, consisting essentially of less than 50 nucleotides and including the 24 nucleotide DNA base sequence

5' CAC TGT CGC TAT GAC AAC ACC GCC 3' or its corresponding RNA base sequence, or their complementary DNA or RNA sequences.

13. The probe of claim 12 consisting essentially of less than 30 nucleotides.

14. The probe of claim 12 consisting essentially of only said 24 nucleotide base sequence.

15. The probe of claim 12 which additionally comprises a label.

16. The probe of claim 15 wherein said label is a radioactive isotope, a fluorescer, a chemiluminescer, or a specifically bindable ligand.

17. An oligonucleotide probe for use in the diagnosis of Alzheimer Disease or a predisposition to develop Alzheimer Disease, consisting essentially of at least 10 nucleotides whose base sequence is homologous with the DNA sequence of the preAPC gene having a mutation in the 24 nucleotide sequence

5' CAC TGT CGC TAT GAC AAC ACC GCC 3', or in its complementary DNA or RNA sequence.

18. The probe of claim 17 consisting essentially of up to 24 nucleotides corresponding to the base sequence of said mutated DNA sequence or its complementary DNA or RNA sequences.

19. The probe of claim 17 which additionally comprises a label.

20. The probe of claim 19 wherein said label is a radioactive isotope, a fluorescer, a chemiluminescer, or a specifically bindable ligand.

* * * * *